US006835808B2

(12) United States Patent
Quentin et al.

(10) Patent No.: US 6,835,808 B2
(45) Date of Patent: Dec. 28, 2004

(54) ANTI-HEPARIN PEPTIDES

(75) Inventors: Gérard Quentin, Yevres (FR); Florence Laur, Paris (FR)

(73) Assignee: Diagnostica-Stago, Asnieres (FR)

( * ) Notice: Subject to any disclaimer, the term of this patent is extended or adjusted under 35 U.S.C. 154(b) by 0 days.

(21) Appl. No.: 10/344,754

(22) PCT Filed: Aug. 14, 2001

(86) PCT No.: PCT/FR01/02610

§ 371 (c)(1),
(2), (4) Date: Apr. 4, 2003

(87) PCT Pub. No.: WO02/14353

PCT Pub. Date: Feb. 21, 2002

(65) Prior Publication Data

US 2003/0171539 A1 Sep. 11, 2003

(30) Foreign Application Priority Data

Aug. 17, 2000 (FR) .......................................... 00 10682

(51) Int. Cl.$^7$ ................................................ A61K 38/00
(52) U.S. Cl. ...................................... 530/323; 530/330
(58) Field of Search ............................. 514/12, 30, 13; 530/324, 325, 326, 358, 329, 330, 323

(56) References Cited

FOREIGN PATENT DOCUMENTS

| EP | 0 325 874 B1 | 4/1992 |
| EP | 0 999 219 A2 | 10/2000 |
| WO | WO 95 13083 A | 5/1995 |
| WO | WO 95/13083 A1 | 5/1995 |
| WO | WO 97 47312 A | 12/1997 |
| WO | WO 97/47312 A1 | 12/1997 |

OTHER PUBLICATIONS

Casu, Benito, "Structure and Biological Activity of Heparin," *Advances in Carbohydrate Chemistry and Biochemistry*, 1985, pp. 51–134, vol. 43.

Van Boeckel, et al., "The Unique Antithrombin III Binding Domain of Heparin: A Lead to New Synthetic Antithrombotics," *Angewandte Chemie*, Dec. 1993, pp. 1671–1818, vol. 32, No. 12.

Lormeau, et al., "The Effect of the Synthetic Pentasaccharide SR 90107/ORG 31540 on Thrombin Generation Ex Vivo Is Uniquely due to ATIII–Mediated Neutralization of Factor Xa," *Thrombosis and Haemostasis*, 1995, pp. 1474–1477, vol. 74, No. 6.

Mayo, et al., "Heparin Binding to Platelet Factor–4," *Biochem, J.*, 1995, pp. 357–365, vol. 312.

Doutremepuich, Christian, "Low Molecular Weight Heparins in Clinical Practice," 1992, pp. 7–12, Marcel Dekker, Inc.

McKay, et al., "Rainbow Trout Protamines," *Eur. J. Biochem*, 1986, pp. 361–366, vol. 158.

Felix, Kurt, Protamines, pp. 1–56, Germany.

Jacques, et al., "Protamine—Antagonist to Heparin," *C.M.A. Journal*, May 19, 1973, pp. 1291–1297, vol. 108.

Cundall, et al., "Interaction of Acridine Orange and Polyanions : Fluorimetric Determination of binding Strengths and the Influence of Simple Electrolytes," 1979, pp. 879–884, vol. 11, No. 2.

Racanelli, et al., "Biochemical and Pharmacologic Studies on the Protamine Interactions with Heparin, Its Fractions and Fragments," *Seminars In Thrombosis and Hemostasis*, 1985, pp. 176–189, vol. 11, No. 2.

Harrow, Jan Charles, "Protamine: A Review of its Toxicity," *Anesth Analg*, 1985, pp. 348–61, vol. 64.

Cook, et al., "Platelet Factor 4 Efficiently Reverses Heparin Anticoagulation in the Rat Without Adverse Effects of Heparin–Protamine Complexes," *Circulation*, Mar. 1992, pp. 1102–1109, vol. 85, No. 3.

Weiler, et al., "Serious adverse reactions to protamine sulfate: Are alternatives needed?" *J. Allergy Clin. Immunol.*, Feb. 1985, pp. 297–303, vol. 75, No. 2.

Wakefield, et al., "Impaired Myocardial Function and Oxygen Utilization Due to Protamine Sulfate in an Isolated Rabbit Heart Preparation," *Ann. Surg.*, Oct. 1990, pp. 387–394.

Teien, et al., "Evaluation Of An Amidolytic Heparin Assay Method: Increased Sensitivity By Adding Purified Antithrombin III," *Thrombosis Research*, 1977, pp. 399–410, vol. 10, No. 3, Pergamon Press, Great Britain.

Delucia, et al., "Efficacy and toxicity of differently charged polycationic protamine–like peptides for heparin anticoagulation reversal," *Journal of Vascular Surgery*, Jul. 1993, pp. 49–60, vol. 18, No. 1.

*Primary Examiner*—Robert A. Wax
*Assistant Examiner*—Robert B. Mondesi
(74) *Attorney, Agent, or Firm*—Foley & Lardner LLP

(57) ABSTRACT

The invention concerns a compound exhibiting an anti-heparin activity, of formula $ZB_{¿}m?(AXA)_xB_{¿}n?(AXA)_yB_o(AXA)_zB_p$, the diagnostic reagents comprising it and the use of said compound in an in vitro diagnostic test of a medicine for anti-heparin activity.

3 Claims, 1 Drawing Sheet

ANTI-HEPARIN PEPTIDES

Figure 1:
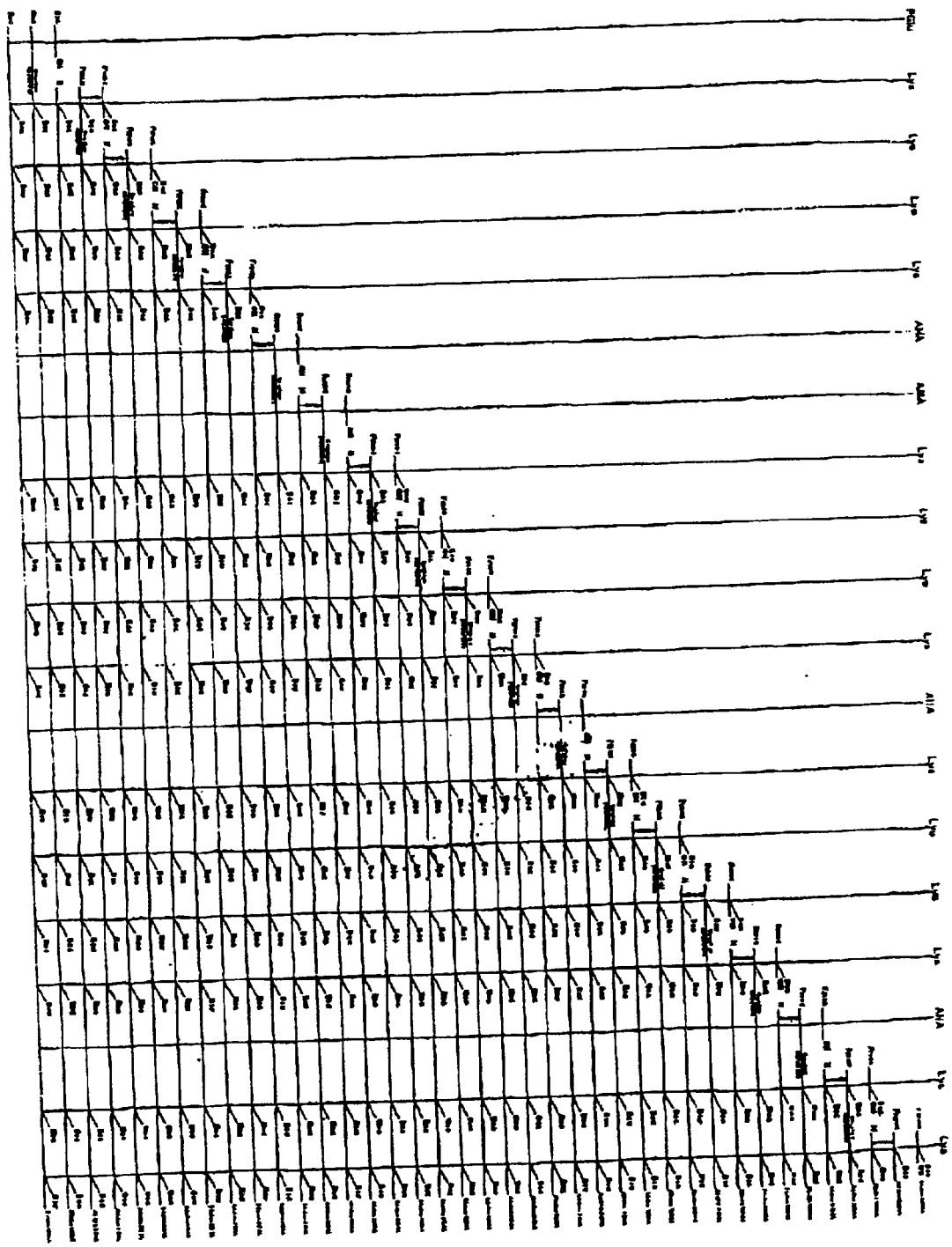

The present invention relates to a compound exhibiting anti-heparin activity, of formula $Z\text{-}B_m\text{-}(AXA)_x\text{-}B_n\text{-}(AXA)_y\text{-}B_o\text{-}(AXA)_z\text{-}B_p$, to the diagnostic reagents comprising it and to the use of said compound in an in vitro diagnostic test or for producing a medicinal product for anti-heparin purposes.

Unfractionated heparin (UFH) is a natural sulfated polysaccharide of the glycosaminoglycan family. It is extracted essentially from pig or bovine intestinal mucosa.

It is a product which is heterogeneous by virtue of the composition of its saccharide units; as a result, the ionic charge of the molecule is also heterogeneous: different degree of sulfation of the glucosamine sulfate units and number of carboxylic functions different in the iduronic and glucuronic acid units [1, 2].

The essential physical characteristics of heparin are: its polyanionicity and its high charge density. Specifically, each disaccharide carries 3 to 4 negative charges (sulfates and carboxylates).

A particular arrangement of the various units of heparin forms the pentasaccharide reproducibly throughout the entire length of the sequence. This pentasaccharide is known to be the antithrombin III recognition site of heparin, generating between these two entities a high affinity and, consequently, a high anticoagulant activity [3].

The chains containing no pentasaccharide are virtually devoid of anticoagulant activity (only ⅓ of the heparin molecule exhibits this affinity for ATIII) [4].

Unfractionated heparin (UFH) is a polydisperse macromolecule: commercial UFH-based preparations have a molecular weight of between 12 000 and 18 000 Da.

These preparations are mainly used for the purpose of preventive or curative action against thromboses.

It is possible to fractionate UFH by size (after chemical treatment), which produces the family of LMWHs (low molecular weight heparins) [5].

UFH has equivalent activity on factors IIa and Xa. On the other hand, LMWHs maintain a high anti-Xa activity and an anti-IIa activity which decreases with the size of the LMWH molecule.

Since a high anti-IIa activity may have hemorrhagic side effects, the LMWHs can be used advantageously as anticoagulants in place of UFHs.

However, the use of UFH or LMWH heparins in therapy may require the administration of compounds which neutralize their anticoagulant effect, in particular at the end of interventions on the circulation system, such as extracorporeal circulation for example. Moreover, in certain diagnostic tests in vitro, the presence of heparin in the samples may lead to erroneous interpretations of the results. It therefore proves to be necessary to also have compounds with anti-heparin properties for diagnosis.

Protamine sulfate is the only known compound capable of neutralizing the anticoagulant effects of heparin in vivo. Protamine belongs to the family of arginine residue-rich basic proteins, is purified from salmon sperm [6–7] and neutralizes heparin by virtue of its positive charges [8–10].

However, protamine causes hemodynamic and hematologic side effects such as hypotension, bradycardia, thrombocytopenia and leukopenia [11–15]. Specifically, it has been demonstrated that the positive charges on protamine are directly proportional to the efficacy and neutralization of heparin, but also to the toxicity of the molecule [16].

Poly (L)-lysine and polybrene are other compounds known to neutralize heparin. However, these polycations also appear to be too toxic for clinical use.

Wakefield et al. (WO 95/13083) describes protamine variants which are thought to be less toxic. They are peptides having a 20 to 40 amino acid sequence, with a positive charge of between +14 and +18, and the structure of which corresponds to clusters of positive residues interspersed with neutral amino acids. Harris et al. (EP 999219) describes linear or branched anti-heparin peptides comprising a succession of arginine and alanine clusters.

However, the abovementioned documents do not comprise any teachings regarding the need to have anti-heparin agents in diagnosis.

A subject of the present invention is novel synthetic molecules which are of use as heparin-neutralizing agents.

The properties of the molecules of the present invention have been more particularly studied in reagents of in vitro diagnosis. Besides their ability to be insensitive to the effects of the heparin possibly present in the blood samples tested, it may also be necessary for some of these diagnostic reagents to exhibit low turbidity. This property is particularly important in the case of reagents containing thromboplastin for determining the Quick time, in particular on automated devices with optical detection.

The molecules having general formula I explained below make it possible to satisfy these two criteria. They therefore prove to be of particular use in neutralizing the possible interference associated with the presence of heparin, both for diagnostic and for therapeutic purposes.

Thus, the present invention relates to a compound exhibiting anti-heparin activity, of general formula I below:

$$Z\text{-}B_m\text{-}(AXA)_x\text{-}B_n\text{-}(AXA)_y\text{-}B_o\text{-}(AXA)_z\text{-}B_p$$

in which

Z has the general formula:

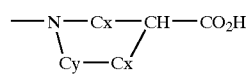

with Cy=-covalent bond
—CH$_2$—
—CO—
—CO—S—
—(CH$_2$)$_n$—X—
with $1 \leq n \leq 2$ and X=O—, S—,

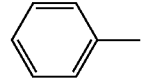

with Cx=-covalent bond
—(CH$_2$)$_n$—, $1 \leq n \leq 5$
or

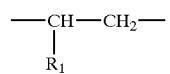

with R1=—OH, —NH$_2$

B represents a basic amino acid and can advantageously be selected from lysine, arginine, ornithine, histidine, homolysine and homoarginine; m, n, o and p represent, independently of one another, an integer of between 2 and 4.

Among the preferred compounds of the invention, the compounds in which m, n and o are equal to 4 and p is equal to 2 are more particularly noted.

AXA represents a hydrocarbon-based chain corresponding to the formula:

—NH—(CH$_2$)$_n$—CO—, n being an integer of between 2 and 6;

x, y and z represent, independently of one another, an integer of between 1 and 6.

Advantageously, Z is selected from the following compounds:

| | | |
|---|---|---|
| Apc | 4-Aminopyrrolidine-2-carboxylic acid | 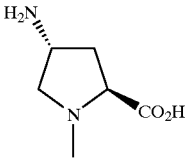 |
| Aze | Azetidine-2-carboxylic acid | 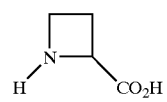 |
| Cop | 2-Carboxymorpholine acid | 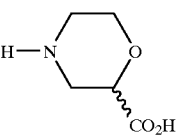 |
| Disc | 1,3-Dihydro-2H-isoindolecarboxylic acid | 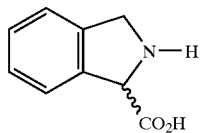 |
| Hyp | Hydroxyproline 4-Hydroxypyrrolidine-2-carboxylic acid | 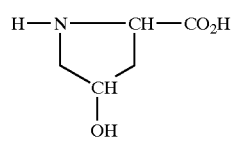 |
| Inc | Indoline-2-carboxylic acid | 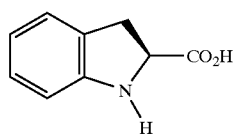 |
| Inp | Isonipecotic acid | 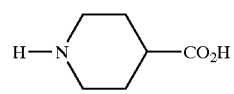 |
| PGlu | Pyroglutamic acid 2-Pyrrolidone-5-carboxylic acid | 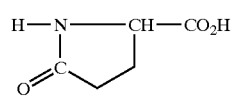 |
| Pip | Pipecolic-2-carboxylic acid | 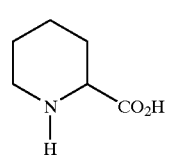 |

-continued

| | | |
|---|---|---|
| Pro | Proline Pyrrolidine-2-carboxylic acid | 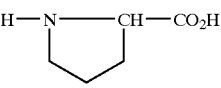 |
| THC | 2-Oxothiazolidine-4-carboxylic acid | 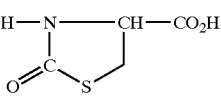 |
| Thi | Thioproline Thiazolidinecarboxylic acid | 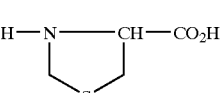 |
| Tiq | Tetrahydroisoquinoline-2-carboxylic acid | 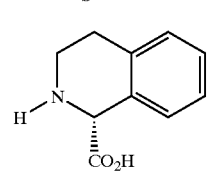 |

Preferably, Z is pyroglutamic acid (PGlu).

Among the preferred compounds of the invention, the compounds in which AHA corresponds to NH—(CH$_2$)$_5$—CO—, i.e. aminohexanoic acid with x equal to 2, and y and z equal to 1, are more particularly noted.

Advantageously, the invention is directed toward the compound corresponding to the following formula:

PGlu-K$_4$-(AHA)$_2$-K$_4$-AHA-K$_4$-AHA-K$_2$

The compounds described above exhibit an anti-heparin capacity, determined by the Δ relative clotting time between a heparinized plasma and a nonheparinized plasma, of less than 10%, preferably less than 5%.

A subject of the present invention is therefore also the use of a compound corresponding to formula 1 indicated above, in a reagent for in vitro diagnosis, in particular reagents for calculating the clotting time of a blood sample, or detecting or assaying various elements of the clotting cascade, independently of the presence or absence of heparin in said sample.

Said reagents, in particular reagents of the PT (prothrombin time) type, advantageously exhibit a turbidity, measured by an OD at 630 nm, of less than 0.5, preferably less than 0.1.

According to another aspect, the invention relates to a reagent for in vitro diagnosis, comprising a compound as defined by general formula 1 above, preferably a compound in which AXA corresponds to NH—(CH$_2$)$_5$—CO—, i.e. hexanoic amino acid, with x equal to 2, and y and z equal to 1, and more preferentially the compound below of formula:

PGlu-K$_4$-(AHA)$_2$-K$_4$-AHA-K$_4$-AHA-K$_2$

Such a diagnostic reagent thus makes it possible to carry out tests or assays in blood samples, independently of the presence or absence of heparin in said samples.

A reagent according to the invention advantageously corresponds to conventional clotting tests, i.e. tests for determining the clotting time of a blood sample, or to tests for detecting or assaying various elements of the clotting cascade, such as, for example, assaying factor VIIa, fibrinogen, and proteins C and S, the PT test. These tests are commonly used by those skilled in the art.

A preferred reagent for in vitro diagnosis according to the invention is a reagent comprising thromboplastin, for carrying out a PT (prothrombin time or Quick time) test.

The final concentration in such reagents of the compound according to the invention defined above is advantageously between 2 and 10 µg/ml.

Preferably, this concentration is 5 µg/ml.

The invention also relates to the use of a compound of general formula 1 defined above, as an anti-heparin agent for preparing a medicinal product.

EXAMPLE 1

Protocol for Synthesizing the Preferred Compound of the Invention

The synoptic table of FIG. 1 summarizes the various steps of the synthesis.

The structural chain is synthesized by solid-support chemistry, using a suitable automated device (Applied Biosystems 433A).

In order to make up the synthetic yield, the hydrophobic spacer arms (AXA) were added by double coupling.

The resin used is an MBHA (methyl benzyhydrylamine) resin, so as to recover a neutral amide C-terminal structure after cleavage from the resin.

The chemistry used here is Fmoc chemistry, using piperidine for deprotection at each step.

The side chains are protected with Boc groups.

The scale of synthesis of the synthesizer is 0.1 nmole, producing approximately 100 mg of crude product. The product is cleaved from the resin and deprotected on the side chains by treatment with TFA (55% trifluoroacetic acid). After concentration of the cleavage solution by 2/3 of the volume, the product is precipitated from ether.

The crude product is subsequently lyophilized and then purified by reverse-phase HPLC, using a 5 µm Kromasil C18 column (20 mm×250 mm) with a gradient of water/acetonitrile 0.1% of TFA (from 0 to 60% acetonitrile in 30 min at 15 ml/minute).

Detection is carried out at 214 nm and the fractions are collected manually.

The amount of purified product recovered is 50 mg.

The structure of the final product is confirmed by analysis of the sequence after hydrolysis with 6N HCl at 120° C. for 24 h; the hydrolyzate is then analyzed by reverse-phase HPLC (Kromasil C18 column, 5 µm, 250 mm×4.6 mm), after derivatization with PITC (phenylthioisocyanate).

EXAMPLE 2

Test for Anti-Heparin Agents According to the Invention on a PT Test

The aim is to analyze the performance (anti-heparin power and turbidity) of anti-heparin agents incorporated into a Diagnostica Stago thromboplastin reagent.

Analysis of the anti-heparin power: This is the ability of the anti-heparin agent to make the reagent insensitive to the heparin contained in the blood sample:

The test samples are prepared from a pool of normal plasma which may or may not be overloaded with heparin (plasma heparinized with 1 IU/ml of UFH (Calciparine 25 000 IU/ml, Sanofi)).

Comment: a reagent serving as a negative control, i.e. without anti-heparin agent, is of use to verify the heparinization of the plasma.

To determine the Quick Time, the automated device (STA Diagnostica Stago—patent EP 0325874) removes 50 µl of sample plasma, which it allows to incubate at 37° C. for 240 seconds in a cupule containing a bead; it then transfers the cupule into the measuring area and adds 100 µl of thromboplastin reagent to the sample.

The clotting time was determined in the following way: At constant viscosity, the amplitude of oscillation of the bead in the cupule (oscillation maintained using an electromagnetic field) is constant. When the viscosity increases (clotting phenomenon), the amplitude of oscillation of the bead decreases.

An algorithm uses this variation in amplitude to determine the clotting time.

The anti-heparin power is calculated in the following way: determination of the delta relative time between a heparinized and nonheparinized plasma, i.e.:

$$[\{CT(\text{heparinized plasma}) - CT(\text{nonheparinized plasma})\}/TC(\text{nonheparinized plasma}) \times 100]$$

with CT=clotting time

The anti-heparin power of the compounds according to the invention is estimated to be significant when this delta time is less than 10%.

Analysis of Turbidity:

The turbidity should be as low as possible for an application in diagnosis, and more particularly in a thromboplastin test (PT).

This turbidity is determined by measuring the OD at 630 nm on a spectrophotometer (Uvikon 940, Kontron).

Comment: a reagent serving as a negative control, i.e. without anti-heparin agent, is of use to measure the influence of this anti-heparin agent on the turbidity of the reagent.

EXAMPLE 3

Analysis of the Performance (Anti-heparin Power and Turbidity) of Various Anti-heparin Agents According to the Invention, Introduced into a Thromboplastin-type Reagent (Results Compared to the Control (C) Having no Anti-heparin Agent)

|  |  | Anti-heparin agent at 5 µg/ml | |
|---|---|---|---|
|  |  | Anti-UFH power Delta time 0/1 IU/ml (in %) | Turbidity OD 630 nm |
| C |  | 99.2 | 0.047 |
| 1415-5 | PGlu-$K_4$-$(AHA)_2$-$K_4$-AHA-$K_4$-AHA-$K_2$ | 4.5 | 0.069 |
| 1415-4 | THC-$K_4$-$(AHA)_2$-$K_4$-AHA-$K_4$-AHA-$K_2$ | 5.9 | 0.148 |
| 1415-3 | Hyp-$K_4$-$(AHA)_2$-$K_4$-AHA-$K_4$-AHA-$K_2$ | 3.4 | 0.134 |
| 1415-2 | Thi-$K_4$-$(AHA)_2$-$K_4$-AHA-$K_4$-AHA-$K_2$ | 5.7 | 0.104 |
| 1394 | Pro-$K_4$-AHA-$K_4$-APA-$K_3$-APA-$K_3$ | 6.4 | 0.399 |
| 1401 | Pro-$K_4$-AHA-$K_4$-APA-$K_4$-APA-$K_2$ | 8.1 | 0.488 |
| 1403P | Pro-$K_3$-AHA-$K_4$-APA-$K_4$-APA-$K_2$ | 7.1 | 0.205 |
| 1403PK | Pro-$K_3$-AHA-$K_4$-APA-$K_4$-APA-$K_2$ | 8.7 | 0.283 |
| 1404 | Pro-$K_4$-AHA-$K_3$-APA-$K_3$-APA-$K_2$ | 7.6 | 0.147 |
| 1405 | Pro-$K_4$-$(AHA)_2$-$K_4$-AHA-$K_4$-AHA-$K_2$ | 4.2 | 0.323 |
| 1408-2 | Pro-$K_4$-AHA-$K_3$-APA-$K_4$-APA-$K_3$ | 6.9 | 0.040 |
| 1411 | Pro-$K_4$-$(AHA)_2$-$K_4$-AHA-$K_3$-AHA-$K_2$ | 6.5 | 0.086 | with APA corresponding to amino propanoic acid, of formula $NH_3$—$(CH_2)_2$—CO—.

REFERENCES

1. Casu, B. (1985) Adv. Carbohydr. Chem. 43: 51–134
2. Constanta, et al. (1993) Angewandte Chemie, Vol. 32, No. 12, 1671–1818
3. Lormeau, H., et al. (1995) Thromb. Haemostasis 74: 1474–1477
4. Mayo, K. M., et al. (1995) Biochem. J. 312: 357–365
5. Mardiguian, J. (1992) Ed. Doutremepuich ch. Marcel Dekker inc. 7–12
6. McKay, D. J., et al. (1986) Eur., J. Biochem. 158: 361–266
7. Kurt, F. (1973) Protamines, Institut für Vegetative Physiologie, Frankfurt, Germany
8. Jacques, L. B. (1973) Can. Med. Assoc. J. 108: 1291–1297
9. Cundall, R. B., et al. (1979) J. Chem. Soc. Perkins Trans. II:879
10. Racanelli, A., et al. (1985) Semin. Thromb. Hemostasis 11: 176–189
11. Horrow, J. C. (1985) Anesth. Analg. 64: 348–361
12. Cook, J. J., et al. (1992) Circulation 85: 1102–1109
13. Weller J. M., et al. (1985) J. Allergy. Clin. Immunol. 75: 297–303
14. Wakefield T. W., et al. (1990) Ann. Surg. 212: 387–395
15. Telen A. N., et al. (1977) Thromb. Res. 10, 399–410
16. DeLucia, A., et al. (1993) J. Vasc. Surg. 10: 49–58

What is claimed is:

1. A compound exhibiting anti-heparin activity comprising the formula:

$$Z\text{-}K_m\text{-}(AXA)_x\text{-}K_n\text{-}(AXA)\text{-}K_o\text{-}(AXA)\text{-}K_2$$

in which

Z has the general formula:

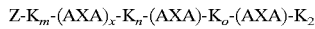

with
Cy=-covalent bond
—$CH_2$—
—CO—
—CO—S—
—$(CH_2)_n$—X—
with $1 \leq n \leq 2$ and X=O—, S—,

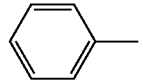

with Cx=-covalent bond
or

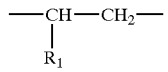

with R1=—OH,—$NH_2$
K represents lysine;
m is 2, 3, or 4; x is 1 or 2; n is 3 or 4; o is 3 or 4; and wherein AXA is AHA or APA.

2. The compound of claim 1, wherein the compound exhibiting anti-heparin activity has the formula of any one of the following anti-heparin agents 1415-5 PGlu-$K_4$-$(AHA)_2$-$K_4$-AHA-$K_4$-AHA-$K_2$,
1415-4 THC-$K_4$-$(AHA)_2$-$K_4$-AHA-$K_4$-AHA-$K_2$,
1415-3 Hyp-$K_4$-$(AHA)_2$-$K_4$-AHA-$K_4$-AHA-$K_2$,
1415-2 Thi-$K_4$-$(AHA)_2$-$K_4$-AHA-$K_4$-AHA-$K_2$,
1394 Pro-$K_4$-AHA-$K_4$-APA-$K_3$-APA-$K_3$,
1401 Pro-$K_4$-AHA-$K_4$-APA-$K_4$-APA-$K_3$,
1403P Pro-$K_2$-AHA-$K_4$-APA-$K_4$-APA-$K_2$,
1403PK Pro-$K_3$-AHA-$K_4$-APA-$K_4$-APA-$K_2$,
1404 Pro-$K_4$-AHA-$K_3$-APA-$K_3$-APA-$K_2$,
1405 Pro-$K_4$-$(AHA)_2$-$K_4$-AHA-$K_4$-APA-$K_2$,
1411 Pro-$K_4$-$(AHA)_2$-$K_4$-AHA-$K_3$-AHA-$K_2$.

3. The compound of claim 1, wherein the compound exhibiting anti-heparin activity has the formula, Pro-$K_4$-$(AHA)_2$-$K_4$-AHA-$K_4$-AHA-$K_2$.

* * * * *